United States Patent
Dykes

Patent Number: 5,951,579
Date of Patent: Sep. 14, 1999

[54] INCISION GUIDE FOR INTRA-OCULAR SURGERY

[76] Inventor: Ronald E. Dykes, 6 Thorncreek Ct., The Woodlands, Tex. 77381

[21] Appl. No.: 08/947,451

[22] Filed: Oct. 6, 1997

[51] Int. Cl.$^6$ .............................. A61F 09/00; A61B 17/32
[52] U.S. Cl. ........................... 606/166; 606/167; 606/107
[58] Field of Search ................................ 606/1, 107, 166, 606/167, 171, 174

[56] References Cited

U.S. PATENT DOCUMENTS

| | | | |
|---|---|---|---|
| 4,499,898 | 2/1985 | Knepshield et al. | |
| 4,515,457 | 5/1985 | Fedorov et al. | |
| 4,520,815 | 6/1985 | Marinoff | |
| 4,534,348 | 8/1985 | Fedorov et al. | |
| 4,637,393 | 1/1987 | Ray | |
| 4,665,914 | 5/1987 | Tanne | |
| 4,674,503 | 6/1987 | Peyman et al. | |
| 4,688,570 | 8/1987 | Kramer et al. | |
| 4,705,037 | 11/1987 | Peyman et al. | |
| 4,763,651 | 8/1988 | Kaufman et al. | |
| 4,768,509 | 9/1988 | Grosvenor et al. | |
| 4,908,015 | 3/1990 | Anis | 604/22 |
| 4,955,894 | 9/1990 | Herman | 606/167 |
| 4,961,744 | 10/1990 | Kilmer et al. | 606/166 |
| 5,224,950 | 7/1993 | Prywes | 606/166 |
| 5,250,062 | 10/1993 | Hanna | 606/166 |
| 5,254,128 | 10/1993 | Mesa | 606/167 |
| 5,336,235 | 8/1994 | Myers | 606/166 |
| 5,336,236 | 8/1994 | Neyas-Wallace | 606/167 |
| 5,370,652 | 12/1994 | Kellan | 606/166 |
| 5,391,177 | 2/1995 | Schwartz | 606/167 |
| 5,411,510 | 5/1995 | Fugo | 606/166 |
| 5,411,511 | 5/1995 | Hall | 606/166 |
| 5,423,330 | 6/1995 | Lee | |
| 5,423,841 | 6/1995 | Kornefled | 606/166 |
| 5,431,671 | 7/1995 | Nallakrishnan | 606/167 |
| 5,437,657 | 8/1995 | Epstein | 606/4 |
| 5,447,517 | 9/1995 | Steen et al. | 606/167 |
| 5,458,610 | 10/1995 | Feaster | 606/166 |
| 5,484,447 | 1/1996 | Waldock et al. | 606/107 |
| 5,486,188 | 1/1996 | Smith | 606/166 |
| 5,496,339 | 3/1996 | Koepnick | 606/166 |
| 5,505,722 | 4/1996 | Kilmer et al. | 606/1 |
| 5,571,124 | 11/1996 | Zelman | 606/166 |
| 5,607,437 | 3/1997 | Simon et al. | 606/166 |
| 5,611,805 | 3/1997 | Hall | 606/166 |
| 5,626,594 | 5/1997 | Smith | 606/166 |
| 5,658,303 | 8/1997 | Koepnick | 606/166 |
| 5,665,099 | 9/1997 | Polo et al. | 606/167 |
| 5,674,233 | 10/1997 | Dybbs | 606/166 |
| 5,690,641 | 11/1997 | Sorensen et al. | 606/107 |
| 5,690,657 | 11/1997 | Koepnick | 606/166 |
| 5,697,945 | 12/1997 | Kritzinger et al. | 606/161 |
| 5,700,274 | 12/1997 | Feaster | 606/167 |
| 5,766,198 | 6/1998 | Li | 606/166 |

FOREIGN PATENT DOCUMENTS

| | | | |
|---|---|---|---|
| 2595243 | 9/1987 | France | 606/166 |
| 3522998 | 1/1987 | Germany | 606/166 |
| 93/20763 | 10/1993 | WIPO | 606/166 |

*Primary Examiner*—Glenn K. Dawson
*Attorney, Agent, or Firm*—Matthews, Joseph, Shaddox & Mason, P.L.L.C.; Matthew E. Burr

[57] ABSTRACT

A surgical aid apparatus and methods for making corneal incisions are disclosed. The apparatus includes a stabilizer pivotally mounted on a body which slidably houses a keratome.

18 Claims, 5 Drawing Sheets

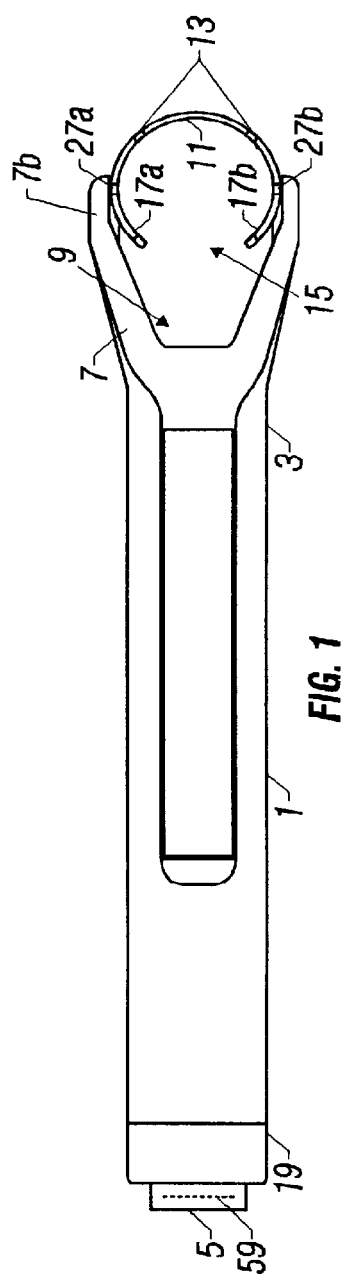
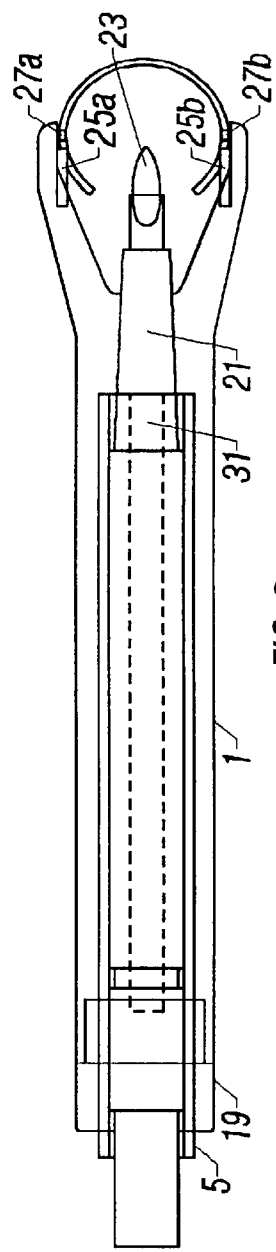
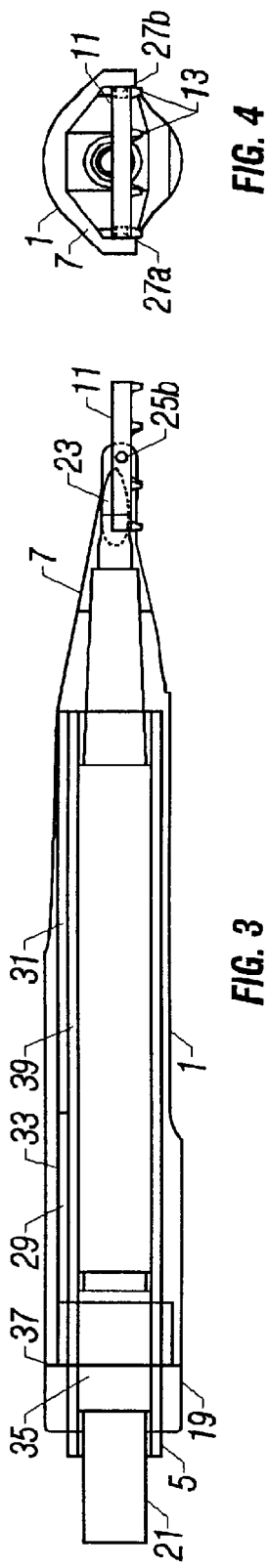

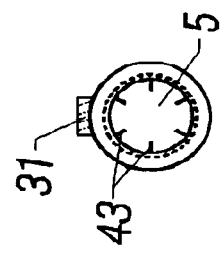
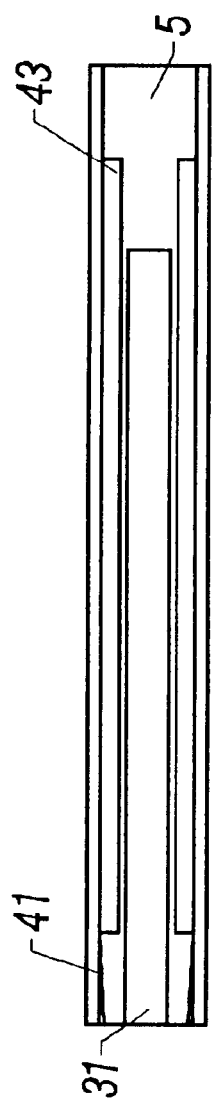
FIG. 6
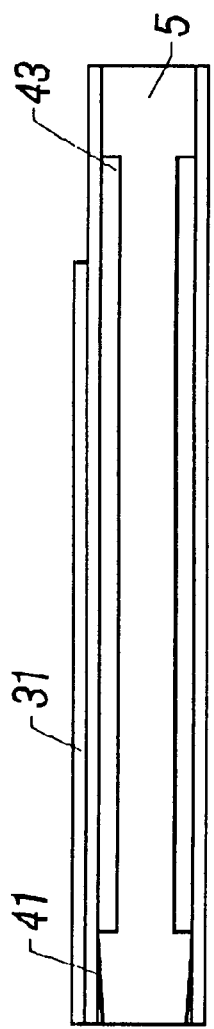
FIG. 7
FIG. 8

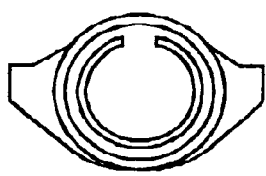
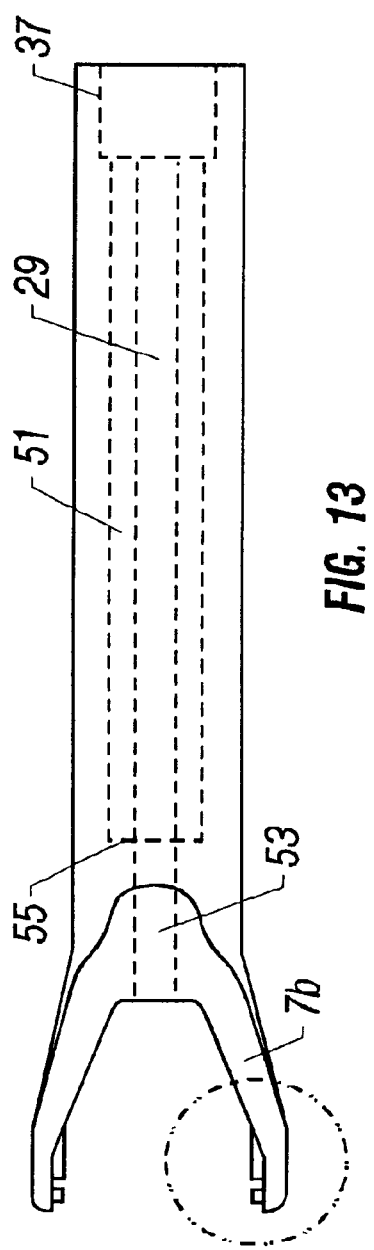
FIG. 13
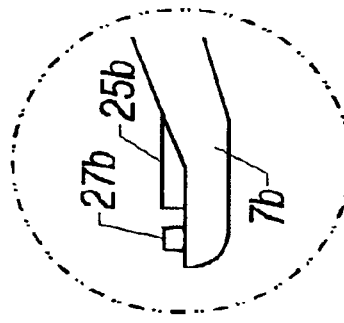
FIG. 14

INCISION GUIDE FOR INTRA-OCULAR SURGERY

TECHNICAL FIELD

The invention relates to an incision guide surgical device, specifically a device that improves the control of incising the eye for intra-ocular surgery. The invention further relates to the methods of use for cataract surgery.

BACKGROUND ART

Cataract surgery is one of the most common surgical procedures performed in the United States. The term "cataract" refers to any opacification of the natural crystalline lens in the eye. Cataracts cause loss of vision. Cataracts are commonly treated by surgically removing the lens from the eye and replacing the natural lens with an artificial lens that restores the vision.

The eye, or eyeball, is roughly spherical in shape. The shape of the eyeball is maintained by an opaque tissue membrane called the sclera, which constitutes the posterior five sixths of the eyeball. The cornea constitutes the remaining one sixth and is positioned at the anterior portion of the eye. The cornea is the transparent anterior portion of the eyeball that extends out from the globe forming a small dome. The outer surface of the cornea is protected by a layer of cells called the corneal epithelium. The bulbar conjunctiva (hereinafter conjunctiva), covers the sclera and is attached at the corneoscleral limbus. The cornea is essentially contiguous with the sclera and the transition from the sclera to the cornea is defined by the corneoscleral junction or limbus. The iris, the colored part of the eye, is a muscular diaphragm in front of the lens. The iris divides the chamber between the lens and the cornea into two chambers: the anterior chamber between the iris and the cornea, and the posterior chamber between the iris and the lens. The lens is held in position in the eyeball by the lens capsule and the lens has a nucleus in its center surrounded by cortex.

In order to remove a cataract, an entry or incision must be made into the eye. Typically two incisions are made. The surgeon first makes a small incision (1.0 mm to 1.5 mm) through the cornea into the anterior chamber to introduce a protective gel (viscoelastic). This maintains the shape of the eye while protecting the posterior portion of the cornea.

The second incision is more complex and is typically 2.5 mm to 3.2 mm in width. The length of this incision varies from 1.75 mm to 3.0 mm depending on surgeon preference and placement of the incision. The second incision begins with the conjunctiva being dissected with scissors to allow exposure of the sclera and placement of a groove. Hemostasis is performed using some type of cautery or diathermy. A groove is then made in the sclera. The sclera is then dissected into the cornea using some type of tunneling blade. At this point a keratome or second surgical blade is introduced into the incision and entry is made through the cornea parallel to the iris, into the anterior chamber of the eye (2.5 mm to 3.2 mm). This incision allows the surgeon to remove the anterior capsule of the lens and, using a method of extraction called phacoemulsification, remove the nucleus of the lens.

Irrigation/aspiration is then used to remove the cortex, leaving the capsular bag in place. The incision is then enlarged and additional viscoelastic is introduced into the capsular bag (the lens membrane emptied of its nucleus and cortex material). The artificial lens is then implanted into the capsular bag and the viscoelastic is removed. The sclera is sutured and the conjunctiva is tacked down using a cautery or diathermy.

A small number of surgeons have developed an advanced technique using a foldable intra-ocular lens and performing a clear corneal incision that eliminates the dissection, diathermy, the enlarging of the incision, and the suturing of the incision described. This technique promotes quicker visual recovery, decreases surgically induced astigmatism and reduces operating time.

Typically, the clear corneal incision is made freehand, using a diamond or metal keratome of varying widths depending on the surgeons needs. A keratome is a surgical instrument consisting of a blade and a handle used for making an incision in the cornea. The blade is mounted on one end of the instrument and held by the surgeon at the other end. The width of an incision is determined by the dimensions of the blade mounted on the keratome. The length of the incision is determined by where the surgeon chooses to enter the anterior chamber.

To make a clear corneal incision under the prior art, a surgeon uses two separate instruments, one held in each hand. The eye is fixated with one hand using forceps or other fixation devices such as a Fine-Thornton Fixation Ring. The other hand holds the keratome to make a freehand incision in the eye. Because of the dome shape of the cornea, the surgeon must estimate the angle at which to introduce the keratome into the cornea. Too steep an angle will create an excessively long tunnel where it is difficult to maneuver instruments, and creates stria which makes it difficult to visualize. Too shallow an angle will create a very short tunnel which will not seal as well and may give pathogens such as bacteria access into the eye. The ideal incision would be located at the corneoscleral limbus and be 1.50 mm to 2.00 mm in length, self sealing, and reproducible.

The incision guide of the present invention combines two prior art instruments into a single instrument and eliminates the guess work involved in determining the optimal angle at which to introduce the keratome into the cornea. The present incision guide places a keratome (or surgical blade) in optimal position at the corneoscleral limbus and at the optimal angle at which to introduce the keratome into the cornea.

Freehand surgery requires a very high skill level, entailing a training or transitional educational phase in which the surgeon acquires the skills necessary to produce a consistent result using trial and error. For the transitioning surgeon, it is particularly difficult to control the plane and speed at which the keratome blade enters the anterior chamber. Variables such as lateral movement due to eye movement, tremor, or other causes can result in incisions that vary in size, shape, and integrity, and may effect the final visual outcome. The present invention eliminates the need for freehand surgery, thereby rendering such variables less significant for the surgeon in training.

In the accomplished surgeon's hands, the described freehand corneal incision has become the state of the art incision for performing cataract surgery. Because of the possible complications associated with any surgical training, a large number of surgeons have chosen not to adopt this new technique. The present invention, however, comprises a fixation device coupled with a surgical blade guide, which enables surgeons to make the transition to corneal incisions while greatly reducing or eliminating the possible complications associated with this training transition.

Even experienced freehand eye surgeons encounter the common problem of overshooting when introducing the blade into the anterior chamber. Overshooting is due to diminished resistance. When the blade begins to enter the anterior chamber, resistance is lost as the blade moves from a dense media, corneal tissue, into a less dense media aqueous humor. Inability to recover from the sudden loss of resistance causes the blade to go beyond the ideal mark. This creates a rectangular incision, not a trapezoid. The desired incision is, ideally, trapezoid shaped; that is, narrow distally and wider proximally, so that an instrument inserted into the cornea through the incision may be manipulated without causing stria or stretching of the corneal tissue. The incision guide of the present invention eliminates the problem of overshooting.

Prior art instruments include fixation devices and fixation devices coupled with a surgical blades. Such instruments were designed to be used in radial keratotomy (a procedure used to correct myopia) and keratectomy (a procedure used to remove a portion of the cornea), but not for cataract surgery or enter into the anterior chamber. Although these instruments are intended to make precise and reproducible incisions, they differ in purpose and design from that of the present invention. The object of prior art instruments is to either prevent entering the anterior chamber while making arcuate or radial incisions of varying depths or to completely remove a segment of the cornea. Prior art inventions are designed to create a pivoting or dragging cutting movement of a surgical blade that makes either an arcuate or radial type incision.

The present invention reproducibly positions the surgical blade at the corneoscleral limbus at the proper angle for an optimal cataract incision and guides the surgical blade while creating a controlled entry into the anterior chamber of the eye. The present invention guides a surgical blade along an axis perpendicular to the cornea and parallel to the iris to create a penetrating longitudinal incision in the cornea. Prior to the present invention this type of incision could only be produced freehand by an accomplished surgeon with extensive experience.

SUMMARY OF THE INVENTION

The present invention is a cornea incision guide to position a surgical blade in proper position for cataract surgery to make controlled, reproducible corneal incisions. For reference, the portion of the guide which is placed on the eye is the distal or forward end of the guide. The portion posterior to the distal end is the proximal or rear end of the guide.

The incision guide comprises a housing for a keratome. To those skilled in the art, it is understood that the keratome carries a blade at the distal end of the keratome handle. The housing comprises a generally tubular body which retains a generally tubular internal sleeve slidably received therein. The body is essentially a tube with an interior surface and an exterior surface, a top and a bottom. The interior surface of the body is formed to comprise a groove to stabilize the internal sleeve.

The internal sleeve holds a keratome and is also a tube having an exterior surface and an interior surface, a top and a bottom. The exterior surface of the internal sleeve is formed to comprise a ridge which fits cooperatively into the groove of the interior surface of the body, to stabilize the sleeve from excessive rotation in relation to the body, and to permit the internal sleeve to slide forward and backward within the body along the groove. The ridge and groove coupling of the sleeve and body allows for approximately 15° of clockwise or counterclockwise rotation of the sleeve within the body so that the surgeon may adjust the position of the blade as required by the surgery being performed.

About 30° rotational play (15° to each side) is permitted by the ridge and groove coupling. A notch is provided at the proximal end of the sleeve to assist the surgeon in aligning the keratome properly within the sleeve. It is recommended to mark the keratome handle to match the notch to avoid trial and error in the alignment.

A yoke is formed from or attached to the distal end of the body. The yoke is substantially Y-shaped, having two prongs which extend distally and slightly laterally from the body of the guide. Pivotally attached to the yoke is a stabilizing ring or device which fixatedly seats on the globe of the eye around the cornea. The stabilizing ring stabilizes the guide on the eye. The stabilizer has a top and a bottom, and the bottom is placed on the eye. The ring is open where it connects to the yoke to permit the blade to be moved forward into the space defined by the ring. Two spurs of the stabilizer, formed by the opening of the ring, extend proximally to the pivoting mount and engage pivot stops on the prongs of the yoke. It will be clear to those skilled in the art that any suitable means for stabilizing the incision guide of the present invention may be utilized, but a substantially circular form is preferred because a circular form permits quick visual verification that the stabilizer is properly aligned on the eye.

The bottom of the stabilizer may have grippers to hold the stabilizer in position on the eye. The grippers may be small teeth, prongs, or protuberances spaced around the bottom of the stabilizer. Even adhesive capable of gripping the supporting tissue to stabilize and fix the apparatus to the eye might be suitable.

The yoke has a bottom side that is substantially flat and parallel to the body of the guide, and a top side that angles downward, terminating at the proximal end of the yoke. Formed with or attached to the top of each prong of the yoke, proximal to the mounting of the ring stabilizer, is a pivot stop that engages the proximal spurs of the stabilizer ring and prevents the stabilizer ring from pivoting out of the desired position for making an incision. The stops may comprise small flats or pins or other suitable structures which extend into the fork of the yoke far enough to engage the proximal spurs of the stabilizer ring and stop the pivotal movement of the pivotable stabilizer when the proximal spurs of the stabilizing ring encounter the stops. With the stabilizer in position on the eye, the stops permit the body of the guide may be pivoted about a range of approximately 90°, from generally perpendicular to the iris to substantially parallel to (or, actually, in substantially the same plane as) the iris. The stops are positioned on the yoke prongs such that the keratome blade within the guide can be reliably positioned in the same plane as the iris of the eye to be incised when the stabilizer is in proper position.

The body comprises stops for stopping the forward and backward motion of the blade at pre-determined positions and to prevent the keratome from moving too far forward toward the eye, and to prevent the inner sleeve from moving too far backward when the keratome is retracted from the eye. The sleeve can move forward and backward in the body by means of a ridge and groove mechanism described above.

A retaining cap or end piece inserts into the proximal end of the body. The end piece is a tube comprising a proximal orifice that allows the internal sleeve to slidably move forward and back in the body and through the orifice of the end piece. The end piece, however, does not have the groove present in the body, and thereby provides a stop to prevent the internal sleeve from falling out of the body when the ridge of the internal sleeve encounters the end piece. The end piece is formed to fit snugly in the body and to be held in place thereby. In the preferred embodiment, the end piece is tapered to ensure a secured fit within the body on the incision guide.

The groove in the interior surface of the body ends at the distal end of the body, approximately where the yoke begins, to stop the internal sleeve from moving too far forward. The groove, therefore, in conjunction with the end piece and the external sleeve, provides stops to prevent excessive forward or backward movement of the internal sleeve carrying the keratome.

Formed from the interior surface of the internal sleeve are small lateral ridges spaced circumferentially around the interior surface for stabilizing a keratome. These stabilizing ridges may be tapered to extend further into the bore of the sleeve at their distal end in order to provide a more secure grip on the keratome as the keratome is moved forward in the sleeve, and to provide a more reliable engagement of the sleeve and the keratome, as the ridges are compressed by the keratome handle. Preferably, the keratome blade comprises diamond and further, an E series trapezoid designed diamond blade. The E series allows a planar incision to be made without the need to dimple down. The trapezoid incision is preferred because of its unique shape: the internal or distal aspect of the incision is smaller than the external or proximal aspect.

In operation of the present invention, the keratome and inner sleeve are initially retracted within the body, with the fragile diamond blade being protected by the body from damage due to inadvertent contact with a second instrument or other object. The inner sleeve and keratome therein, therefore, extend out of the orifice of the end piece in position to be slid forward to move the blade into the tissue when the blade is in proper position relative to the eye.

The stabilizing ring is place around the cornea of the eye with the grippers facing down securing the ring in place on the eye. The eye is approached with the stabilizer from a position generally perpendicular to the plane of the iris so that proper positioning can be gauged as the ring is put in place on the eye. The body of the guide is lowered or pivoted into a horizontal orientation, substantially parallel to plane of the iris, while maintaining the stabilizer in position on the eye. The flat portion on the bottom of the yoke allows the body of the guide to be pivoted into parallel position without the curvature of the distal portion of the substantially tubular body obstructing the positioning of the guide into parallel position. In this position, the blade is perpendicular to the edge of the cornea and parallel to the plane of the iris.

To make the incision, the keratome is slid forward, engaging the inner sleeve and moving the inner sleeve forward also. The cooperative ridge and groove structure of the sleeve and the body stabilizes the blade so that it cannot rotate more than 15° to either side in relation to the plane of the iris. The blade is moved forward and enters the cornea at the limbus and parallel to the iris. Forward movement of the keratome should be stopped once the first set of shoulders of the blade have entered the anterior chamber, and the blade should then be withdrawn. The result is an identical incision that is made every time. The keratome is retracted back into the guide to complete the incision and the stabilizer is removed from the eye.

By creating a stabilizing device coupled to a guide that correctly aligns the surgical blade so as to make an incision into the anterior chamber that is located at the corneoscleral limbus and is 1.75 mm to 2.25 mm in length, self sealing and reproducible, the present invention solves the problem of possible complications associated with surgical training transition to make a corneal incision for intra ocular surgery and makes it possible to create a precise and reproducible incision.

Because of its preciseness and reproducibility, further application of the present invention include the ability to create incisions that can be examined for optimum width, length and placement to determine their strength and ability to self seal.

An additional benefit is in cost savings for those who use diamond surgical blades. By having the sleeve secure the diamond surgical blade into the body which is attached to the fixation device, it prevents damage to the diamond which can otherwise occur when a second instrument is used to fixate the globe and the diamond is allowed to come in contact with it.

BRIEF DESCRIPTION OF THE DRAWINGS

Other objects and advantages of this invention will become apparent from the following description and accompanying drawings wherein;

FIG. 1 is a bottom view of the present invention.

FIG. 2 is a cross-sectional view top of the present invention. This view also includes a diamond surgical blade of the preferred embodiment.

FIG. 3 is a cross-sectional side view of the present invention. This view also shows a keratome carrying a surgical blade within the body of the preferred embodiment.

FIG. 4 is a front view of the present invention.

FIG. 6 is a top view of the inner sleeve of the present invention.

FIG. 7 is a cross-sectional side view of the inner sleeve of the present invention.

FIG. 8 is a front view of the of the internal sleeve of FIG. 7.

FIG. 13 is a cross-sectional top view of the body of the present invention.

FIG. 14 is a top view detail of one prong of the body of FIG. 13.

DETAILED DESCRIPTION OF THE PREFERRED EMBODIMENT

Figure 5:
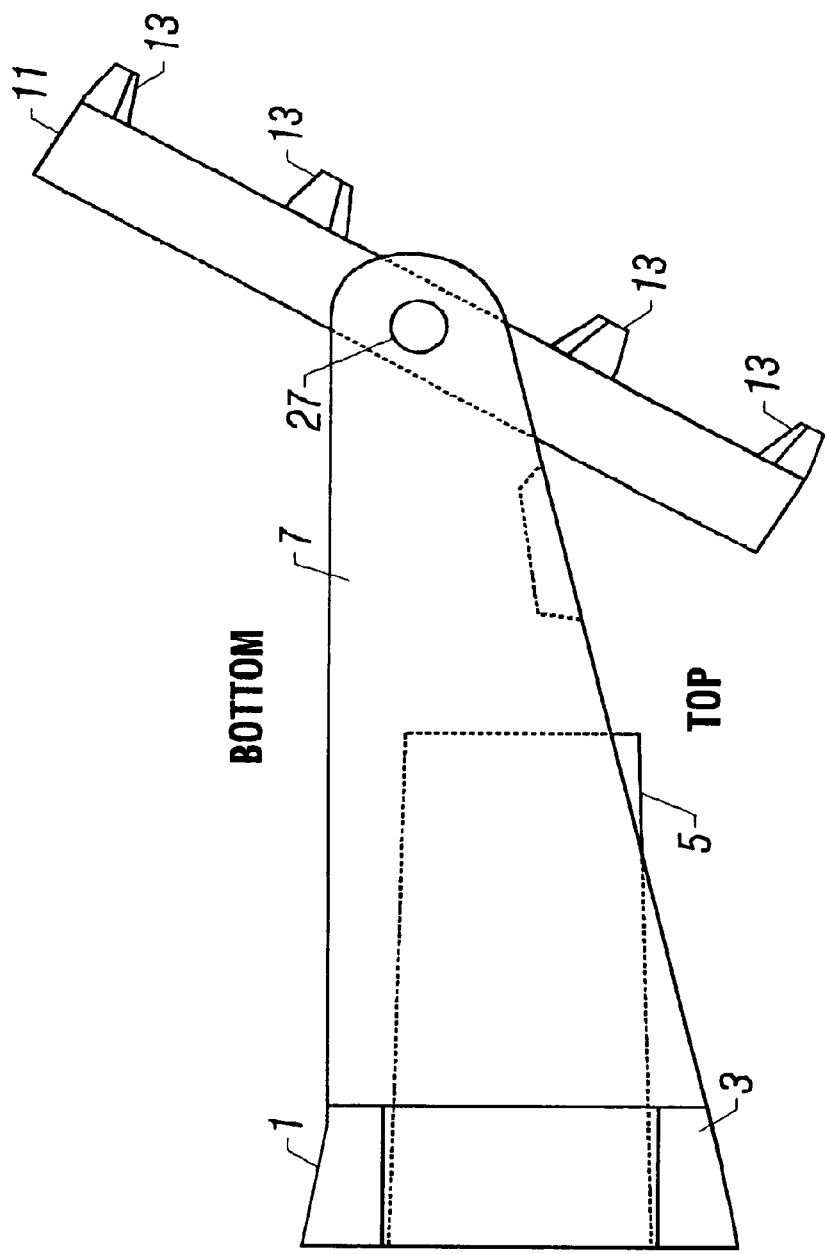
FIG. 5 is a side view showing stabilizing ring in position to place on the eye.

Referring now to FIG. 1, a bottom view of the preferred embodiment of the present invention is shown. The incision guide 1 is comprised of body 3 and internal sleeve 5 housed therein. The body 3 comprises a tube which combines distally with yoke 7. Yoke 7 is comprised of two prongs 7a and 7b, forming void 9 between said prongs. Stabilizing ring 11 is attached to yoke 7 with pivoting mount 27a and 27b at prongs 7a and 7b, respectively. Stabilizing ring 11 further comprises spaced grippers 13 on the bottom side as a means for securing the incision guide on the eye. Ring 11 is actually an open ring, having an arcuate or U-shape comprising opening 15 proximal to said pivotal mount. Spurs 17a and 17b extend proximal to said pivoting mount. A portion of internal sleeve 5 protrudes from the open proximal end of body 3, and also from end piece 19, mounted on the proximal end of body 3. Notch 59 in sleeve 5 at the proximal end helps align a keratome properly within sleeve 5.

Said pivotal mount comprises a pin 27 situated at the distal end of each prong 3a,b of yoke 7. Stabilizing ring 11 comprises a hole on each side capable of receiving the pins 27 on yoke 7 to form a pivoting mount for the stabilizing ring and permitting the ring to pivot about the pin-in-hole mount.

As shown in FIG. 2, a keratome 21 is seated within sleeve 5. Blade 23 is mounted on the distal end of keratome 21, shown here extended forward into space 15 of stabilizing ring 11.

Continuing with FIG. 2, the top side of Yoke 7 further comprises stops 25a and 25b on each prong 7a and 7b, respectively, proximal to pivotable mount 27a and 27b, to stop the pivotal movement of stabilizing ring 5 in the proper position for fixing the stabilizing ring on the eye and for pivoting the guide into position for making an incision. Stops 25a and 25b may comprise small, generally wedge-shaped flats or shelves extending into the void 9 defined by yoke 7 sufficiently to make contact with the spurs 17a and 17b of stabilizing ring 11 proximal to pivotable mountings 27a and 27b.

FIG. 3 is a cross-sectional side view of the embodiment of FIG. 2. Groove 29, formed from interior surface 33 of body 3, accepts ridge 31, formed from the exterior surface 35 of internal sleeve 5. The proximal end of body 3 is shaped to comprise a female receptacle 37 to accept male end piece 19, the distal end of which is shaped to comprise a male portion 39 complimentary to receptacle 37. Groove 29 extends proximally from the proximal end of receptacle 37 to the beginning of yoke 3 distally. Ridge 31 extends along the top of sleeve 5 from the distal end of sleeve 17 to approximately the midpoint of sleeve 5 proximally. Groove 29, therefore, is longer than ridge 31, thereby allowing internal sleeve 5 to slide forward and backward within the body 3. Groove 29 and ridge 31 further cooperate to stabilize internal sleeve 5 from excessive twisting rotation inside the body 3 (no more than 30° of rotation).

When sleeve 5 is moved backward far enough, ridge 31 runs into the distal end of end piece 19, and sleeve 5 is thereby stopped from sliding out of the proximal end of sleeve 3.

The top 61 of yoke 7 angles down and terminates at the end of prongs 7a and 7b. The bottom 63 of the yoke 7 is substantially flat and recessed from the circumference of the body. Surface 63, being flat and recessed, allows the body to be pivoted over the eye without the otherwise tubular shape of the body obstructing the proper positioning of the present incision guide about the eye.

FIG. 4 is a front view of the incision guide of the present invention, illustrating the alignment of the body 1 with the stabilizing ring 11 in position to make an incision.

FIG. 5 illustrates the incision guide of the present invention with the body 3 of the guide pivoted about mount 27 with the stabilizing ring 11 in position to place on the eye. Stabilizing ring 11 is placed on the eye with the grippers 13 in contact with the eye around the iris. The body of the incision guide is pivoted downward until the body and ring are in the position depicted in FIGS. 1–4 for making an incision.

FIG. 6 is a cross-sectional top view of internal sleeve 5 showing top ridge 31. The interior surface 41 of sleeve 5 is slightly tapered, being wider at the proximal end and narrower at the distal end, to provide a snug fit for a keratome, and to provide means for stopping said keratome from being moved too far forward inside the body 3 when making an incision. Interior ridges 43 for gripping and stabilizing a keratome seated within sleeve 17 are spaced around the circumference of interior surface 41. Interior ridges 43 are similarly tapered to provide a reliable grip on the keratome.

FIG. 7 shows ridge 25 of internal sleeve 5 in a side view cross section.

FIG. 8 is a front view of sleeve 5, showing ridge 31 on top extending from the exterior surface 33 of sleeve 5, and interior ridges 43 for gripping and stabilizing a keratome seated within sleeve 5.

Figure 9:
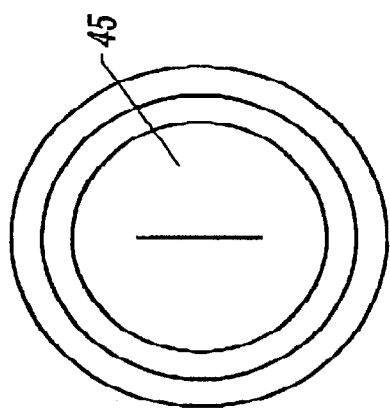
FIG. 9 is a cross-sectional view of the end piece of the present invention.

FIG. 9 illustrates a front distal view of end piece 19. End piece 19 is generally tubular, comprising a bore 45 there through having substantially the same internal diameter as body 3.

Figure 10:
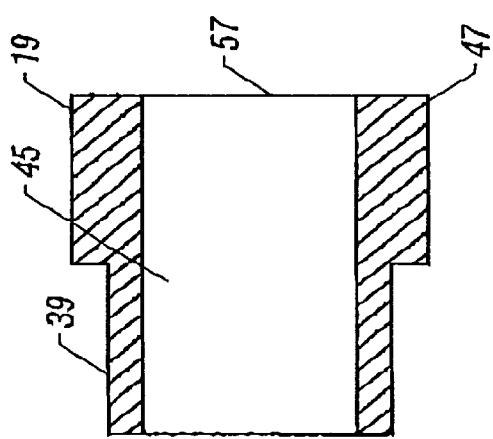
FIG. 10 is a cross-sectional side view of the end piece of FIG. 9.

FIG. 10 shows a cross-sectional side view of the end piece of FIG. 9. The diameter of the interior surface of bore 45 is the same through the length of the bore and terminates proximally at orifice 57. The exterior surface comprises two outer diameters. A small outer diameter 39 at the distal end of end piece 19 forms the male fitting to fit within the proximal female receptacle 37 of body 3. A larger outer diameter 47 at the proximal end of end piece 19 forms the end cap of the present invention.

Figure 11:
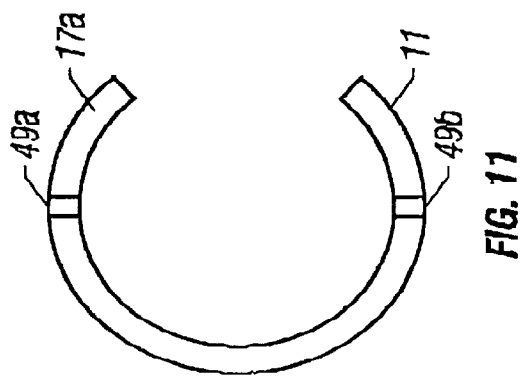
FIG. 11 is a cross-sectional top view of the stabilizing ring of the present invention.

FIG. 11 is a cross-sectional top view of stabilizing ring 11 showing holes 49a and 49b into which insert pins 27a and 27b on yoke 7 to form the pin-in-hole pivoting mount. Proximal spurs 17a and 17b catch on stops 25a and 25b mounted distally to pins 27a and 27b on yoke 5 to stop excessive pivoting of ring 11.

Figure 12:
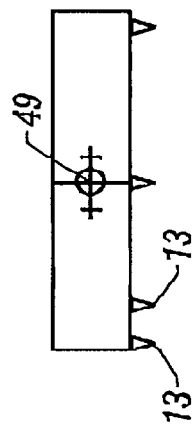
FIG. 12 is a side view of the stabilizing ring of FIG. 11.

FIG. 12 is a side view of ring 11, illustrating the placement of hole 49 for the pivoting mount, and grippers 13 on the bottom of ring 5.

FIG. 13 shows body 3 in cross-sectional top view. Receptacle 37 is formed from the proximal end of sleeve 3 to accommodate end piece 19. Groove 29 extends from receptacle 37 to approximately yoke 7. The interior surface 33 forms a series of annuluses of diminishing diameter from the proximal end to the distal end. Receptacle 37 is the widest annulus. The main bore 51 of sleeve 3 follows groove 29 to comprises another annulus; in fact groove 29 is formed from top surface of bore 51. The narrowest annulus 53 begins at the distal end of bore 51 and forms a protective housing for blade 23 when the keratome 21 is retracted back into the incision guide 1. Annulus 53 may be tapered to be narrower distally and wider proximally. Lip 55 between bore 51 and annulus 53 serves as a distal stop for internal sleeve 5.

FIG. 14 is a detail of FIG. 13 showing prong 7b and illustrating pin 27b and stop 25b.

In operation, keratome 21 is fitted with a blade 23 seated in internal sleeve 5 and retracted back into the body 3. Stabilizing ring 11 is pivoted to be approximately perpendicular to yoke 7 (FIG. 5). Stabilizing ring 11 is placed on the eye of a patient so that the bottom of the ring, having grippers 13 for fixating the ring on the eye, is in contact with the eye tissue and secures the ring 11 in proper position around the iris of the eye. The keratome 21 and inner sleeve 5 are initially retracted within the body 3 with the blade 23 protected from damage by the body 3.

The incision guide of the present invention is pivoted toward the patient's face approximately 90° so that the bottom of yoke 7 is substantially parallel to said stabilizing ring 11. In this position, blade 23 is optimally situated to incise the eye at the corneoscleral limbus. The incision is made manually by sliding the keratome 21 toward the cornea. Blade 23 thereby incises the eye above and parallel to the iris at the corneoscleral limbus. The keratome 21 and blade 23 are retracted into the present incision guide 1 leaving a self-sealing incision at the corneoscleral limbus 1.25 mm to 2.25 mm in length.

The present incision guide provides many features to aid the physician in making the ideal corneal incision. The ridge-groove cooperation of the body and internal sleeve operates to guide the blade for optimal incision. The yoke and pivoting stabilizing ring cooperate to ensure that the blade enters the tissue at the optimum angle and position for the desired incision. Use of the preferred diamond blade in the present invention results in quick, highly reproducible, self sealing incisions. The present invention is particularly useful for practitioners with limited experience. The present incision guide eliminates the need for multiple instruments, free hand surgery on the eye, and allows even novices to make ideal, reproducible incisions.

While the preferred embodiment of the present invention has been disclosed, it will be understood by those skilled in the art that various modifications can be made without departing from the spirit and scope of the claimed invention.

What is claimed is:

1. An apparatus for making surgical incisions, and intraocular incisions, the apparatus comprising:
   a blade;
   means for housing said blade;
   means for stabilizing said house on the eye, wherein said stabilizing means comprises pivot means for pivotally mounting said stabilizing means on said housing means;
   means for moving said blade forward and backward within said housing means;
   means within said housing means for stopping said motion forward and backward of said blade at predetermined positions; and
   means for stopping pivoting movement of said stabilizing means at at least one predetermined position;
   whereby said blade is maintained in proper orientation in relation to said housing means and in relation to a desired incision location.

2. The apparatus of claim 1, wherein said housing means comprises:
   a generally tubular body comprising an interior surface, said interior surface comprising means for stabilizing an internal sleeve; and
   a generally tubular internal sleeve slidably fitting within said body and cooperating with said means for stabilizing said internal sleeve, said internal sleeve further comprising an exterior surface, and an interior surface for receiving said blade, said interior surface of said internal sleeve further comprising means for stabilizing said blade within said internal sleeve.

3. The apparatus of claim 2, wherein said means for stabilizing said internal sleeve in said body comprises a groove formed from the interior surface of said body and a cooperating ridge formed from the exterior surface of said internal sleeve, wherein said groove and said ridge slidably engage each other to permit movement of said internal sleeve forward and backward in said body.

4. The apparatus of claim 2, wherein said body comprises a yoke for attaching said means for stabilizing said means for housing said blade.

5. The apparatus of claim 4, wherein said yoke comprises 2 prongs, each prong comprising a pin.

6. The apparatus of claim 2, wherein said means for stabilizing said internal sleeve comprises a cooperating ridge and groove.

7. The apparatus of claim 1, wherein said means for moving said blade forward and backward within said housing means comprises a cooperating groove and ridge.

8. The apparatus of claim 1, wherein said blade is mounted on a keratome and said housing means houses said keratome comprising said blade.

9. The apparatus of claim 1, wherein said means for stabilizing said housing comprises an open ring, said ring being open proximal to said housing means to permit said blade to move into the interior void of said open ring.

10. The apparatus of claim 1, wherein said pivot means comprises a cooperating pin and hole.

11. The apparatus of claim 1, wherein said means within said housing for stopping said motion backward of said blade comprises a removable end piece attached to said housing means.

12. The apparatus of claim 11, wherein said end piece further comprises an orifice, and wherein said blade, and said means for moving said blade forward and backward within said housing means, extend out of said orifice when said blade is retracted in said housing means.

13. The apparatus of claim 1, wherein said blade is a diamond blade.

14. The apparatus of claim 13, wherein said blade is an E series trapezoid diamond blade.

15. The apparatus of claim 1, wherein said housing means comprises a recessed bottom portion to allow proper positioning of said housing means about an eye for making an incision.

16. The apparatus of claim 1, wherein said means for moving said blade forward and backward allows for approximately 15° of rotational movement around either side of said moving means.

17. A method for making a clear corneal incision utilizing an apparatus comprising:
   a blade;
   means for housing said blade;
   means for stabilizing said housing means on the eye, wherein said means for stabilizing is pivotally mounted on said means for housing said blade;
   means for moving said blade forward and backward within said housing means; and
   means within said housing means for stopping said motion of said blade at a (at least one) predetermined position;
   means for stopping pivoting movement of said stabilizing means at predetermined positions;
   whereby said blade is maintained in proper orientation in relation to said housing means and in relation to a desired incision location, the method comprising:
   retracting the blade within the housing means to protect the blade;
   placing the means for stabilizing said housing means securely around the iris of an eye with the housing means forming an angle in relation to the plane of the iris of greater than zero degrees;
   pivoting the housing means so that the blade within the housing is in the desired position in relation to the cornea and the iris;
   moving the blade in the housing means toward and into the cornea, thereby making an incision in the cornea; and
   retracting the blade into the housing means.

18. A surgical apparatus for use with a keratome, the apparatus comprising:
   a sleeve for holding a keratome;
   a body for slidably retaining said sleeve;
   a yoke at the distal end of said body; and
   an open ring pivotally mounted on said yoke.

* * * * *